United States Patent
Hirayama et al.

(10) Patent No.: US 9,839,358 B2
(45) Date of Patent: Dec. 12, 2017

(54) LIGHT PENETRATION DEPTH EVALUATION METHOD, PERFORMANCE TEST METHOD USING EVALUATION METHOD, AND OPTICAL TOMOGRAPHY APPARATUS

(71) Applicant: FUJIFILM Corporation, Tokyo (JP)

(72) Inventors: Heijiro Hirayama, Ashigarakami-gun (JP); Sohichiro Nakamura, Ashigarakami-gun (JP)

(73) Assignee: FUJIFILM Corporation, Minato-ku, Tokyo (JP)

( * ) Notice: Subject to any disclaimer, the term of this patent is extended or adjusted under 35 U.S.C. 154(b) by 0 days.

(21) Appl. No.: 15/496,130

(22) Filed: Apr. 25, 2017

(65) Prior Publication Data

US 2017/0224219 A1 Aug. 10, 2017

Related U.S. Application Data

(63) Continuation of application No. PCT/JP2015/005318, filed on Oct. 22, 2015.

(30) Foreign Application Priority Data

Oct. 27, 2014 (JP) .................................. 2014-218398

(51) Int. Cl.
*G01B 9/02* (2006.01)
*G01B 11/02* (2006.01)
*A61B 5/00* (2006.01)

(52) U.S. Cl.
CPC ............ *A61B 5/0066* (2013.01); *A61B 5/441* (2013.01); *A61B 5/742* (2013.01); *G01B 9/02001* (2013.01); *G01B 9/02091* (2013.01)

(58) Field of Classification Search
CPC ...... G01B 11/02; G01B 9/02; G01B 9/02001; G01B 9/02091
(Continued)

(56) References Cited

U.S. PATENT DOCUMENTS 8,427,653 B2 * 4/2013 Hacker .................. A61B 3/102
356/497
9,562,759 B2 * 2/2017 Vogler .................... A61B 3/102
(Continued)

FOREIGN PATENT DOCUMENTS

| JP | 2006-000385 A | 1/2006 |
| JP | 2008-304314 A | 12/2008 |

(Continued)

OTHER PUBLICATIONS

Wolfgang Drexler, "Ultrahigh-resolution optical coherence tomography," Journal of Biomedical Optics, 2004, pp. 47-74, vol. 9, No. 1.

(Continued)

*Primary Examiner* — Roy M Punnoose
(74) *Attorney, Agent, or Firm* — Sughrue Mion, PLLC

(57) ABSTRACT

Using an optical tomography method of splitting low coherent light into sample light and reference-light, emitting the sample light to a measurement-target in a line shape, generating interference light by superimposing reflected light from the measurement-target due to emission of the sample light and the reference-light on each other, and acquiring a two-dimensional spectroscopic tomographic-image of the measurement-target by spectroscopically detecting the interference light and performing frequency analysis, an arbitrary wavelength region in an ultraviolet region is cut out from low coherent light including a wavelength region from an ultraviolet region to a visible region and the arbitrary wavelength region is shaped into a spectrum having an (Continued)

arbitrary wavelength width, the two-dimensional spectroscopic tomographic-image is acquired as using the low coherent light, and the penetration depth of the sample light for the measurement-target is evaluated based on the two-dimensional spectroscopic tomographic-image.

20 Claims, 11 Drawing Sheets

(58) Field of Classification Search
USPC .......................................................... 356/510
See application file for complete search history.

(56) References Cited

U.S. PATENT DOCUMENTS

2009/0185191 A1* 7/2009 Boppart ............... A61B 5/0066
356/479
2014/0009743 A1 1/2014 Donitzky et al.

FOREIGN PATENT DOCUMENTS

| JP | 2011-179902 A | 9/2011 |
| JP | 2013-108766 A | 6/2013 |
| JP | 2014-506510 A | 3/2014 |
| KR | 1020040081964 A | 9/2004 |

OTHER PUBLICATIONS

Wiel A. G. Bruls et al., "Transmission of Human Epidermis and Stratum Corneum as a Function of Thickness in the Ultraviolet and Visible Wavelengths," Photochemistry and Photobiology, 1984, pp. 485-494, vol. 40, No. 4.
Written Opinion of the International Searching Authority of PCT/JP2015/005318 dated Feb. 23, 2016.
International Search Report of PCT/JP2015/005318 dated Feb. 23, 2016.
Communication dated Oct. 9, 2017 from the European Patent Office in counterpart application no. 15855630.8.

* cited by examiner

LIGHT PENETRATION DEPTH EVALUATION METHOD, PERFORMANCE TEST METHOD USING EVALUATION METHOD, AND OPTICAL TOMOGRAPHY APPARATUS

CROSS-REFERENCE TO RELATED APPLICATIONS

This application is a Continuation of PCT International Application No. PCT/JP2015/005318 filed on Oct. 22, 2015, which claims priority under 35 U.S.C. §119(a) to Japanese Patent Application No. 2014-218398 filed on Oct. 27, 2014. Each of the above applications is hereby expressly incorporated by reference, in its entirety, into the present application.

BACKGROUND OF THE INVENTION

1. Field of the Invention

The present invention relates to a method of evaluating the depth of penetration of light into a measurement target as using an optical tomographic image, a performance test method using the evaluation method, and an optical tomography apparatus.

2. Description of the Related Art

In the development of cosmetics and medicines and in medical care, it is important to observe the condition inside the skin. In Europe, since the sale of cosmetics tested on animals has been completely prohibited in the spring of 2013, there is an increasing need for a method for observing the human skin in a non-destructive and non-invasive manner. It is also important as an industrial management method to measure a multilayered structure, such as a photographic film, in a non-destructive manner with high resolution.

Magnetic resonance imaging (MRI), ultrasound, X-ray Computed Tomography (CT), and Optical Coherence Tomography (OCT) are examples of a non-destructive and non-invasive tomographic imaging method. The measurement depth of MRI, ultrasound, and X-ray CT is mm to cm order, which is deep, but the resolution is 10 µm to 100 µm or more, which is not high. OCT is a tomographic imaging method using optical interference. In general, near-infrared light (wavelength of 1.3 µm or 1.5 µm) is mainly applied to fundus examination and the like.

Since the depth resolution $\Delta z$ of OCT is given by $\Delta z = 2 \times (\ln(2)/\pi) \times (\lambda^2/\Delta\lambda)$, it is possible to increase the resolution by increasing the wavelength width $\Delta\lambda$ of a light source to be used and decreasing the center wavelength $\lambda$ of the light source (where $\lambda$ is the center wavelength of the light source, $\Delta\lambda$ is the wavelength width of the light source, and $\Delta z$ is a resolution in the depth direction). In the near-infrared OCT, the depth resolution is about 20 µm. In recent years, in order to improve the depth resolution, development of OCT using the entire wavelength region from visible to near infrared has been performed (Journal of Biomedical Optics, Vol. 9, (1), pp. 47-74, 2004). In Journal of Biomedical Optics, Vol. 9, (1), pp. 47-74, 2004, the depth resolution has reached submicron order.

JP2013-108766A has proposed a method in which low coherent light of red, green, and blue in the visible region is generated by Super Luminescent Diode (SLD) light sources of respective colors and a foundation is applied to skin replica to evaluate the surface unevenness or the thickness of the foundation layer.

JP2014-506510A has proposed using light in a wavelength range of 300 nm to 500 nm as sample light in order to increase the resolution in the depth direction in a known OCT apparatus for ophthalmology that uses infrared light (wavelength of 800 nm to 1300 nm) as sample light.

In JP2008-304314A, a xenon lamp, a light emitting diode, a super luminescent diode, or a multi-mode laser diode that can respond to a continuous spectrum from the ultraviolet region to the infrared region (wavelength of 185 nm to 2000 nm) is exemplified as a light source.

On the other hand, it is known that, in the case of ultraviolet light (wavelength of 400 nm or less), an effect of eliminating the tension of the skin by making the melanin pigment present in the epidermis of human skin proliferate and damaging the collagen present in the dermis occurs. The depth of penetration of ultraviolet light (hereinafter, also referred to as Ultra Violet (UV) light) into the skin is said to be 50 µm to several hundred µm. In the past study example (Photochemistry and photobiology, Vol. 40, (4), pp. 485-494, 1984), the epidermis of actual human skin is cut out and the transmittance of ultraviolet light is measured while thinly cutting the epidermis while changing the thickness, thereby determining the attenuation rate of ultraviolet light at each thickness.

SUMMARY OF THE INVENTION

In the OCT apparatus disclosed in JP2013-108766A, since an ultraviolet light source is not used, measurement in the ultraviolet region is not possible. In addition, since this is a time domain type (full field type) OCT, mechanical scanning of the sample stage is necessary. Accordingly, this is not suitable for measurement of samples causing blurring, such as human skin. In Journal of Biomedical Optics, Vol. 9, (1), pp. 47-74, 2004, using the fact that the resolution is improved by increasing the wavelength width, OCT measurement is performed as using a broadband light source with a wavelength of 500 nm to 1600 nm. However, OCT measurement in the ultraviolet region is not possible.

In the method disclosed in Photochemistry and photobiology, Vol. 40, (4), pp. 485-494, 1984, since it is necessary to cut the human skin, the burden is large. Accordingly, a method of directly observing the penetration depth of UV light in a non-destructive and non-invasive manner is desired to quantify the effect of cosmetics.

In JP2014-506510A, since the measurement wavelength is fixed to a specific wavelength in the range of 300 nm to 500 nm, it is not possible to compare measurement results and the like between multiple wavelengths.

In JP2008-304314A, a xenon lamp, a light emitting diode, a super luminescent diode, or a multi-mode laser diode that can respond to a continuous spectrum from the ultraviolet region to the infrared region (wavelength of 185 nm to 2000 nm) is exemplified as a light source. However, among these light sources, there is nothing that satisfies the three conditions of spatial coherence, temporal low coherence, and sufficient wavelength width. Accordingly, these light sources are not suitable for being applied to OCT measurement in practice. In addition, since the apparatus disclosed in JP2008-304314A is an OCT using wavelength sweep, this is not an apparatus that can selectively extract arbitrary wavelengths in an optimal spectral shape. Therefore, comparison of tomographic images between different wavelengths is not possible.

The present invention has been made in view of the above circumstances, and it is an object of the present invention to provide a light penetration depth evaluation method capable of evaluating the penetration depth of ultraviolet light for a measurement target in a non-destructive and non-invasive manner, a performance test method using the evaluation method, and an optical tomography apparatus capable of executing a light penetration depth evaluation method.

A light penetration depth evaluation method of the present invention is a light penetration depth evaluation method using an optical tomography method of splitting low coherent light into sample light and reference light, emitting the sample light to a measurement target in a line shape, generating interference light by superimposing reflected light from the measurement target due to emission of the sample light and the reference light on each other, and acquiring a two-dimensional spectroscopic tomographic image of the measurement target by spectroscopically detecting the interference light and performing frequency analysis. The light penetration depth evaluation method includes: cutting out an arbitrary wavelength region in an ultraviolet region from low coherent light, which is emitted from a single light source and which includes a wavelength region from an ultraviolet region to a visible region, and shaping the arbitrary wavelength region into a spectrum having an arbitrary wavelength width; acquiring the two-dimensional spectroscopic tomographic image as using the low coherent light in the arbitrary wavelength region having the spectrum; and evaluating a penetration depth of the sample light for the measurement target based on the two-dimensional spectroscopic tomographic image.

That is, the light penetration depth evaluation method of the present invention is an evaluation method for evaluating the penetration depth of ultraviolet light for the measurement target.

In the light penetration depth evaluation method of the present invention, after the two-dimensional spectroscopic tomographic image based on the low coherent light in the arbitrary wavelength region in the ultraviolet region is acquired as a first two-dimensional spectroscopic tomographic image, a second two-dimensional spectroscopic tomographic image may be acquired by changing an amount of low coherent light in the arbitrary wavelength region. The penetration depth of the sample light for the measurement target may be evaluated based on the first two-dimensional spectroscopic tomographic image and the second two-dimensional spectroscopic tomographic image.

In the light penetration depth evaluation method of the present invention, the arbitrary wavelength region in the ultraviolet region may be set as a first wavelength region, and the two-dimensional spectroscopic tomographic image based on the low coherent light in the arbitrary wavelength region in the ultraviolet region may be set as a first two-dimensional spectroscopic tomographic image. A second wavelength region different from the first wavelength region may be cut out from low coherent light, which is emitted from the single light source and which includes a wavelength region from the ultraviolet region to the visible region, and the second wavelength region may be shaped into a second spectrum having an arbitrary wavelength width. A second two-dimensional spectroscopic tomographic image based on the low coherent light in the second wavelength region having the second spectrum obtained by the shaping may be acquired, and the penetration depth of the sample light for the measurement target may be evaluated based on the first two-dimensional spectroscopic tomographic image and the second two-dimensional spectroscopic tomographic image.

Alternatively, in the light penetration depth evaluation method of the present invention, at the same time as when cutting out an arbitrary wavelength region in the ultraviolet region from low coherent light that is emitted from a single light source and includes a wavelength region from the ultraviolet region to the visible region, a second wavelength region different from a first wavelength region may be cut out and the second wavelength region may be shaped into a second spectrum having an arbitrary wavelength width with the arbitrary wavelength region as the first wavelength region and the spectrum previously obtained by the shaping as a first spectrum. A second two-dimensional spectroscopic tomographic image may be acquired as using low coherent light in the second wavelength region having the second spectrum obtained by the shaping at the same time as when acquiring the two-dimensional spectroscopic tomographic image as a first two-dimensional spectroscopic tomographic image as using low coherent light in the first wavelength region. The penetration depth of the sample light for the measurement target may be evaluated based on the first two-dimensional spectroscopic tomographic image and the second two-dimensional spectroscopic tomographic image.

That is, a light penetration depth evaluation method of the present invention is a light penetration depth evaluation method using an optical tomography method of splitting low coherent light into sample light and reference light, emitting the sample light to a measurement target in a line shape, generating interference light by superimposing reflected light from the measurement target due to emission of the sample light and the reference light on each other, and acquiring a two-dimensional spectroscopic tomographic image of the measurement target by spectroscopically detecting the interference light and performing frequency analysis. The light penetration depth evaluation method may include: cutting out an arbitrary wavelength region from low coherent light, which is emitted from a single light source and which includes a wavelength region from an ultraviolet region to a visible region, and shaping the arbitrary wavelength region into a spectrum having single or plural arbitrary wavelength widths to acquire a first two-dimensional spectroscopic tomographic image, which is based on low coherent light in a first wavelength region in an ultraviolet region, and a second two-dimensional spectroscopic tomographic image, which is based on low coherent light in a second wavelength region different from the first wavelength region or based on low coherent light in the first wavelength region having a light amount different from the low coherent light in the first wavelength region, simultaneously or sequentially; and evaluating a penetration depth of the sample light for the measurement target based on the first two-dimensional spectroscopic tomographic image and the second two-dimensional spectroscopic tomographic image.

In order to acquire the OCT signal, it is necessary to handle light having a wavelength width instead of a single wavelength. Here, it is preferable that the spectrum of light, which is cut out for OCT measurement (acquisition of a two-dimensional spectroscopic tomographic image) and is shaped to arbitrary wavelength and wavelength width, is Gaussian distribution.

In this specification, the ultraviolet region refers to a wavelength range of 200 nm or more and 400 nm or less, and the visible region refers to a wavelength range exceeding 400 nm and equal to or less than 780 nm. However, in this specification, the light in the ultraviolet region that is used for measurement and has an arbitrary wavelength width refers to light having a center wavelength in the range of 200 nm or more and 400 nm or less, and the light in the visible region refers to light having a center wavelength exceeding 400 nm and equal to or less than 780 nm.

That is, the wavelength region cut out from the low coherent light emitted from the light source is regarded as a wavelength region in the ultraviolet region if the peak wavelength obtained by shaping is in the ultraviolet region, and is regarded as a wavelength region in the visible region if the peak wavelength is in the visible region.

Evaluation of the light penetration depth means acquiring information regarding the light penetration depth, which includes at least one of calculation of the light penetration depth based on calculation using an optical tomographic image (data), measurement (visual measurement) of the light penetration depth by visual observation from an optical tomographic image, or comparison of the light penetration depth between a plurality of optical tomographic images.

For the center wavelength and the wavelength width of light, when the spectrum is fitted by the following equation, $x_0$ is the center wavelength and width is the wavelength width.

$$y = y_0 + A \times p(-((x-x_0)/(\text{width}))^2)$$

The second wavelength region may be a wavelength region in the ultraviolet region, or may be a wavelength region in the visible region.

A performance test method of the present invention is a performance test method for testing a performance of chemicals by evaluating a penetration depth of light in an ultraviolet region before and after application of the chemicals to human skin, which is a measurement target, using the light penetration depth evaluation method described above.

Here, the chemicals include cosmetics, medicines, and quasi-drugs.

An optical tomography apparatus of the present invention comprises: a light source unit that has a single light source, which emits low coherent light including a wavelength region from an ultraviolet region to a visible region, and a spectrum shaping unit, which cuts an arbitrary wavelength region in the ultraviolet region from light emitted from the light source and shapes the arbitrary wavelength region into a spectrum having an arbitrary wavelength width, and that emits low coherent light after the spectrum shaping; a light splitting unit that splits the low coherent light emitted from the light source unit into sample light and reference light; a sample light emission optical system that emits the sample light to a measurement target in a line shape; a multiplexing unit that superimposes reflected light from the measurement target when the sample light is emitted to the measurement target and the reference light on each other; an interference light detection unit that spectroscopically detects interference light between the reflected light and the reference light multiplexed by the multiplexing unit; and a tomographic image acquisition unit that acquires a two-dimensional spectroscopic tomographic image of the measurement target by performing frequency analysis of the interference light detected by the interference light detection unit.

It is preferable that the optical tomography apparatus of the present invention further comprises a measurement unit that calculates a penetration depth of the sample light for the measurement target from the two-dimensional spectroscopic tomographic image.

It is preferable that, at the same time as when cutting out an arbitrary wavelength region in the ultraviolet region from low coherent light including a wavelength region from the ultraviolet region to the visible region and shaping the arbitrary wavelength region into a spectrum having an arbitrary wavelength width, the spectrum shaping unit cuts out a second wavelength region different from a first wavelength region and shapes the second wavelength region into a second spectrum having an arbitrary wavelength width with the arbitrary wavelength region as the first wavelength region and the previously shaped spectrum as a first spectrum. It is preferable that the tomographic image acquisition unit acquires a second two-dimensional spectroscopic tomographic image as using low coherent light in the second wavelength region having the second spectrum at the same time as when acquiring the two-dimensional spectroscopic tomographic image as a first two-dimensional spectroscopic tomographic image as using low coherent light in the first wavelength region.

It is preferable that the optical tomography apparatus of the present invention comprises a display unit that displays the two-dimensional spectroscopic tomographic image.

In addition, it is preferable that the sample light emission optical system comprises a variable neutral density filter.

It is possible to adopt a configuration in which the sample light emission optical system comprises a cylindrical lens and a cylindrical lens disposed perpendicular to the cylindrical lens is provided between the multiplexing unit and the interference light detection unit.

It is preferable that the light source is a super continuum light source.

The light penetration depth evaluation method of the present invention is to acquire a two-dimensional spectroscopic tomographic image as using low coherent light, which is obtained by cutting out an arbitrary wavelength region in the ultraviolet region and performing spectrum shaping, and evaluate the depth of penetration of ultraviolet light into the measurement target from the two-dimensional spectroscopic tomographic image. Therefore, it is possible to evaluate the light penetration depth for the measurement target in a non-destructive and non-invasive manner.

According to the performance test method using the light penetration depth evaluation method of the present invention, the ultraviolet protection capability of chemicals can be tested in a non-destructive and non-invasive manner for the measurement target.

DESCRIPTION OF THE PREFERRED EMBODIMENTS

Hereinafter, embodiments of an optical tomography apparatus and a light penetration depth evaluation method of the present invention will be described with reference to the diagrams.

Figure 1:
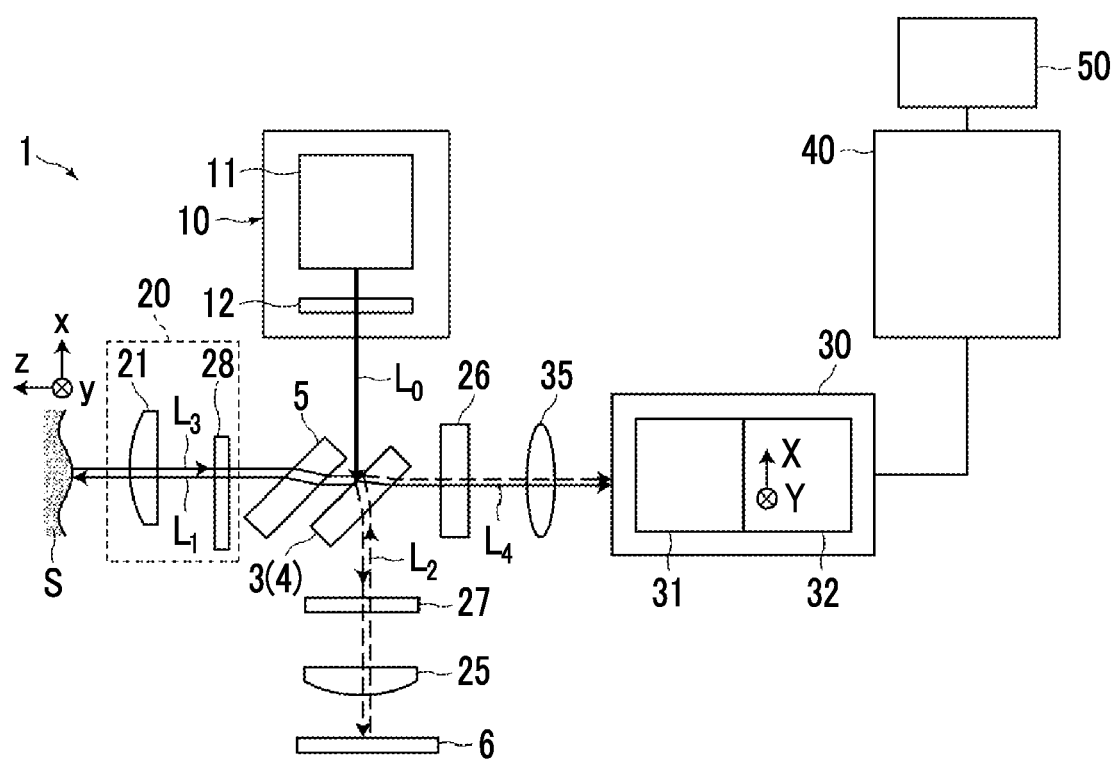
FIG. 1 is a schematic diagram showing the overall configuration of an optical tomography apparatus according to an embodiment of the present invention.

FIG. 1 is a diagram schematically showing the overall configuration of an optical tomography apparatus 1 according to an embodiment of the present invention. As shown in FIG. 1, the optical tomography apparatus 1 of the present embodiment has: a light source unit 10 that emits low coherent light L0; a light splitting unit 3 that splits the low coherent light $L_0$ emitted from the light source unit 10 into sample light $L_1$ and reference light $L_2$; a sample light emission optical system 20 for emitting the sample light $L_1$ to a measurement target S (in this case, human skin) in a line shape; a multiplexing unit 4 for superimposing reflected light $L_3$ from the measurement target S when the sample light $L_1$ is emitted to the measurement target S on the reference light $L_2$; an interference light detection unit 30 that spectroscopically detects interference light $L_4$ between the reflected light $L_3$ and the reference light $L_2$ multiplexed by the multiplexing unit 4; a tomographic image acquisition unit 40 that acquires a two-dimensional spectroscopic tomographic image of the measurement target by performing frequency analysis of the interference light detected by the interference light detection unit 30; and an image display device 50 for displaying the two-dimensional spectroscopic tomographic image.

The light source unit 10 has a single light source 11 that emits light including a wavelength region from an ultraviolet region to a visible region and a spectrum shaping unit 12 that cuts out an arbitrary wavelength region in at least the ultraviolet region from the light emitted from the light source 11 and shapes the arbitrary wavelength region into the Gaussian distribution spectrum of single or plural arbitrary wavelength widths, and emits the low coherent light $L_0$ spectrally shaped in an arbitrary wavelength region.

As the light source 11, a white light source (super continuum light source) that emits super continuum (SC) light is suitable.

The spectrum shaping unit 12 cuts out an arbitrary wavelength region from light in a broad band including the entire ultraviolet to visible region that is emitted from the light source 11, and shapes the arbitrary wavelength region into the Gaussian distribution spectrum of single or plural arbitrary wavelength widths. Specifically, a color filter can be used. The wavelength region cut out by the spectrum shaping unit 12 may be only the wavelength in the ultraviolet region, or may include both the ultraviolet region and the visible region. The region to be cut out may not be a continuous region but may be a plurality of regions separated from each other. The spectrum shaping unit 12 generates a spectrum having at least one peak in the ultraviolet region, such as a spectrum having one or more (for example, two) peaks of the wavelength in the ultraviolet region or a spectrum having a peak in the ultraviolet region and a peak in the visible region. In a spectrum having a plurality of peaks, it is preferable that each peak forms a Gaussian distribution spectral shape. In order to obtain such a spectrum, a multiple wavelength simultaneous transmission filter having a transmission spectrum of a plurality of peaks may be used as the spectrum shaping unit 12.

Here, the spectrum of the wavelength region cut out by the spectrum shaping unit 12 is shaped into the Gaussian distribution spectrum. However, in a spectrum shaping unit, shaping into low coherent light having a spectral shape suitable for spectroscopic tomographic image acquisition is sufficient, and the shape of the spectrum after shaping is not limited to the Gaussian distribution spectrum.

By using coherent light of a spectrum having a plurality of peaks, spectroscopic tomographic images based on low coherent light beams with different peak wavelengths can be simultaneously obtained. As a result, a plurality of spectroscopic tomographic images of a desired combination, such as spectroscopic tomographic images based on low coherent light beams with different peak wavelengths in the ultraviolet region or spectroscopic tomographic images based on low coherent light beams in the ultraviolet region and the visible region can be simultaneously obtained, and light penetration at each wavelength, a difference in light penetration depth due to wavelength difference, and the like can be evaluated.

The intensity of the SC light in the UV range is very small, and the light intensity significantly decreases as the wavelength decreases. For this reason, it is not possible to obtain a Gaussian distribution waveform just by cutting unnecessary light, such as the visible region, with a sharp cut filter. On the other hand, it is possible to obtain a Gaussian distribution waveform by gradually shaping the spectrum by superimposing several filters having a gentle transmittance spectrum. However, due to the loss of light amount due to reflection from the top and bottom surfaces of each filter, the light intensity significantly decreases if several filters are superimposed. For this reason, this is not suitable for OCT measurement. Therefore, it is preferable to specially prepare a filter having a transmittance spectrum so as to have a Gaussian distribution waveform with only one filter, corresponding to the spectrum of the light source.

The larger the wavelength width of the light source, the better in terms of the resolution of the OCT. However, if the wavelength width of the light source is too large, comparison when changing the wavelength is difficult. As a measure of the wavelength width, about several nm to 100 nm is preferable.

Figure 2:
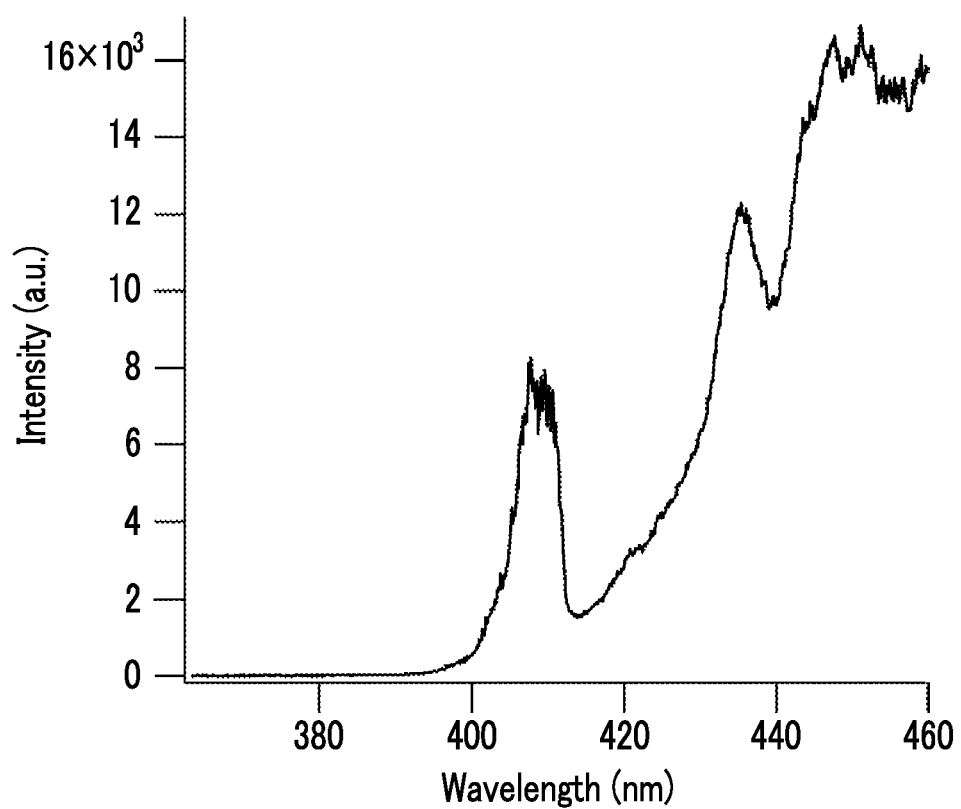
FIG. 2 is a diagram showing the profile of light that is output from a light source and that includes a wavelength region from an ultraviolet region to a visible region.

A specific example will be described. Super continuum light is light including wavelengths ranging from the entire ultraviolet to visible region. For example, the profile of the super continuum light in the wavelength region equal to or less than 460 nm is shown in FIG. 2. The super continuum light used herein has a relatively high intensity at 400 nm or more. However, the intensity in the wavelength region of 400 nm or less is extremely low, and corresponds to the skirt portion of the profile.

Figure 3:
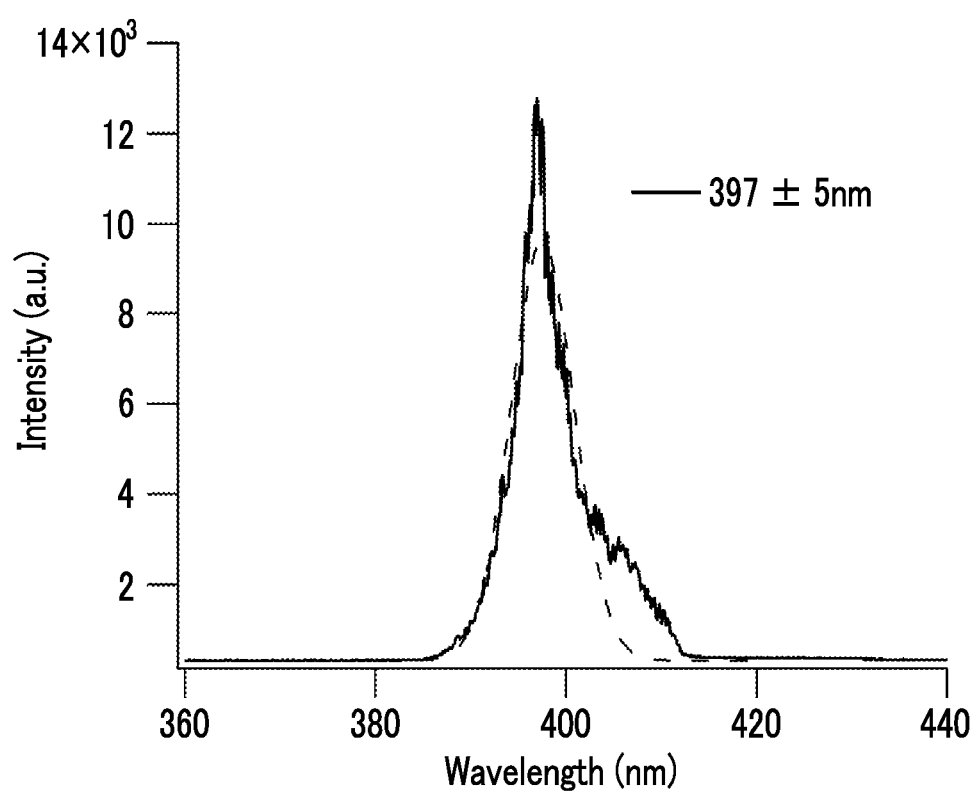
FIG. 3 is a diagram showing a Gaussian distribution spectrum shaped by cutting out a specific wavelength region in an ultraviolet region from light having the profile shown in FIG. 2.

FIG. 3 shows a Gaussian distribution spectral shape having a peak wavelength at 397 nm and a wavelength width of 5 nm from the light shown in FIG. 2. In FIG. 3, the solid line shows an actual spectral shape, and the broken line shows an ideal Gaussian distribution. As shown in FIG. 3, the spectral shape obtained by shaping is not a perfect Gaussian distribution but a shape along the approximate Gaussian distribution. In this specification, for example, the spectrum having a peak wavelength of 397 nm and a wavelength width of 5 nm may be expressed as a spectrum of 397±5 nm.

In the tomography apparatus of the present invention, it is possible to acquire a two-dimensional spectroscopic tomographic image as using low coherent light showing the Gaussian distribution spectrum in the ultraviolet region as shown in FIG. 3.

In the present embodiment, the light splitting unit 3 that separates the low coherent light $L_0$ emitted from the light source unit 10 into the sample light $L_1$ and the reference light $L_2$ is formed by a quartz plate, and the light splitting unit 3 also functions as the multiplexing unit 4 that multiplexes the reflected light $L_3$ of the sample light $L_1$, which is emitted to the measurement target S, and the reference light $L_2$. The quartz plate 3 (4) is configured such that the low coherent light $L_0$ is incident on the incidence surface at a predetermined incidence angle (for example, 45°) that is not 0°, light reflected on the incidence surface of the low coherent light $L_0$ incident on the incidence surface of the quartz plate 3 (4) is emitted to the measurement target S as the sample light $L_1$, and light transmitted through the quartz plate 3 (4) of the low coherent light $L_0$ incident on the incidence surface is incident on a reflecting member 6 as the reference light $L_2$.

As the light splitting unit 3 and the multiplexing unit 4, it is also possible to use a general beam splitter, half mirror, and the like. However, since the quartz plate is inexpensive and the reflected light is very low as about 4%, it is possible to suppress irritation to human skin by using the reflected light as sample light, which is very preferable.

Since a large refractive index dispersion occurs in light that is incident from a direction not perpendicular to the incidence surface of the quartz plate 3 (4) and is emitted from the emission surface opposite to the incidence surface, a quartz plate 5 for dispersion compensation is disposed on the optical path of the sample light $L_1$. The quartz plate 5 for dispersion compensation has the same shape as the quartz plate 3 that is a light splitting unit, and is disposed approximately in parallel to the quartz plate 3.

The sample light emission optical system 20 is provided between the quartz plate 3 (4) and the measurement target S. The sample light emission optical system 20 includes a cylindrical lens 21. By the cylindrical lens 21, the sample light $L_1$ is emitted in a line shape extending in a direction y of one axis (depth direction of the page in FIG. 1) on the surface of the measurement target S. As the cylindrical lens 21, for example, a cylindrical lens having a focal length f=75 mm is provided. By emitting the sample light $L_1$ in a line shape, it is possible to acquire a two-dimensional tomographic image by single exposure in a short period of time.

The sample light emission optical system 20 may include other optical systems, such as a polarizer and a zoom lens (not shown).

The sample light emission optical system 20 includes a variable neutral density (ND) filter 28, so that it is possible to arbitrarily change the amount of sample light to be emitted to the measurement target.

By cutting out arbitrary wavelengths in the ultraviolet region to obtain a Gaussian distribution spectrum and then acquiring a two-dimensional tomographic image by increasing or decreasing the amount of sample light for the same Gaussian distribution spectrum, it is possible to evaluate the penetration depth of ultraviolet light at each light amount or a difference in the penetration depth of ultraviolet light due to a difference in light amount.

In a case where the evaluation of the penetration depth due to the difference in light amount is not performed, the optical tomography apparatus may be configured not to include the variable ND filter. Even in a case where no variable ND filter is provided, it is preferable to provide an ND filter for attenuating the fixed amount of light so as to reduce the amount of ultraviolet light to such an extent that the ultraviolet light does not harm the human body.

The reflecting member 6 is, for example, a mirror, and is disposed so as to reflect the reference light $L_2$ separated by the light splitting unit 3 to the multiplexing unit 4 side.

The multiplexing unit 4 multiplexes the reference light $L_2$ reflected by the reflecting member 6 and the reflected light $L_3$ from the measurement target S and emits the obtained light to the interference light detection unit side. As described above, in the present embodiment, the multiplexing unit 4 is formed by a quartz plate that also serves as the light splitting unit 3.

In order to improve the coherence between the reference light $L_2$ and the reflected light $L_3$, it is necessary that the optical path length, through which the reference light $L_2$ and the reflected light $L_3$ have passed, or the wavelength dispersion characteristic is the same. Therefore, in the present embodiment, for example, a cylindrical lens 25 of f=75 mm, which is the same as the cylindrical lens 21 disposed on the optical path of the sample light $L_1$ (and the reflected light $L_3$), is disposed on the optical path of the reference light $L_2$. The reflected light $L_3$, which is reflected from the measurement target S to return to the multiplexing unit 4, of the sample light $L_1$ emitted to the measurement target S is so small. Therefore, in order to ensure the symmetry between the intensity of the reference light $L_2$ and the intensity of the reflected light $L_3$, a neutral density filter (ND filter) 27 for reducing the intensity of the reference light $L_2$ is provided on the optical path of the reference light $L_2$.

The interference light detection unit 30 spectrally separates the interference light $L_4$ between the reflected light $L_3$ and the reference light $L_2$ multiplexed by the multiplexing unit 4 and detects the interference light $L_4$ for each wavelength component, and includes a spectroscope 31 for splitting the interference light $L_4$ and a two-dimensional photodetector 32.

As the spectroscope 31, various known techniques can be used. For example, the spectroscope 31 can be formed as using a diffraction grating or the like. The photodetector 32 is, for example, a two-dimensional photosensor in which light receiving elements, such as charge coupled devices (CCD) or photodiodes, are arranged in a two-dimensional manner. A method may also be considered in which the interference light $L_4$ is split by a beam splitter or the like and a plurality of spectroscopes or a plurality of CCDs are provided for each of split light beams to simultaneously measure the spectral information.

Between the multiplexing unit 4 and the interference light detection unit 30, a cylindrical lens (focal distance f=150 mm in this example) 26 and an imaging lens (focal distance f=50 mm) 35 are provided as an optical system for guiding the interference light $L_4$ to the interference light detection unit 30.

The cylindrical lens 26 is an objective lens in the y direction disposed such that the axis of the cylinder in the longitudinal direction is perpendicular to the cylindrical lens 21 for performing linear emission that is disposed in the sample light emission optical system 20.

Light receiving elements of the XY-axis two-dimensional photosensor forming the photodetector 32 are arranged in the XY direction schematically shown in the photodetector 32 in FIG. 1, and the spectroscope 31 is disposed such that the interference light $L_4$ is spectrally separated and the amount of light for each wavelength is detected by light receiving elements arranged in the X-axis direction on the two-dimensional photosensor. In the two-dimensional photosensor, interference light due to reflected light for each line direction (y direction) position of the line-shaped sample light on the measurement surface is incident on the light receiving elements arranged in the Y-axis direction. It is possible to obtain information in the depth direction (z direction) by performing a Fourier transform (FT) of light in the x direction compressed by the cylindrical lens 21. That is, in the optical tomography apparatus 1, since light beams having information in one direction (y direction) and depth direction (z direction) on the surface of the measurement target are simultaneously incident on the two-dimensional photosensor, it is possible to acquire an yz two-dimensional spectroscopic tomographic images with one exposure (one shot).

The tomographic image acquisition unit 40 is formed by, for example, a personal computer and a computer program. The tomographic image acquisition unit 40 acquires reflection information at the depth position z of the measurement target S by performing frequency analysis of the interference light $L_4$ detected by the interference light detection unit 30, thereby obtaining a two-dimensional spectroscopic tomographic image. The tomographic image acquisition unit 40 acquires the reflection information at the depth position z of the measurement target S by converting the wavelength into a wave number in the intensity spectrum for each wavelength detected from the light receiving elements arranged in the X-axis direction of the two dimensional photosensor and performing a Fourier transform. In this operation, the depth z can be obtained by FT of the wave number. However, since the depth z at this time is the optical path length corresponding to the refractive index 1, it is necessary to consider the refractive index for the display of the depth z.

The optical tomography apparatus 1 includes an image display device (display unit) 50 for displaying a spectroscopic tomographic image. The image display device 50 can be formed by a liquid crystal display or the like, and the observer can evaluate the depth of light penetration into the measurement target by displaying the spectroscopic tomographic image of the measurement target on the image display device 50. Simultaneously displaying the scale on the spectroscopic tomographic image or in the vicinity of the image makes it easy to visually measure the light penetration depth. The image display device 50 may display the light penetration depth obtained by a measurement unit, which will be described later, simultaneously with the spectroscopic tomographic image or in a sequential manner. The image display device 50 may simultaneously display spectroscopic tomographic images acquired by coherent light beams having different light amounts or different wavelengths that have been acquired simultaneously or sequentially. By simultaneously displaying a plurality of spectroscopic tomographic images, it is possible to easily evaluate a difference in light penetration depth between the plurality of spectroscopic tomographic images.

In the optical tomography apparatus of the present invention, it is preferable to provide a measurement unit for measuring the penetration depth of light from the spectroscopic tomographic image (data). In addition, the measurement unit may be configured to calculate a difference in penetration depth of light between a plurality of spectroscopic tomographic images. Similar to the tomographic image acquisition unit, the measurement unit can be formed by a personal computer and a program installed into the computer.

The optical tomography apparatus of the present invention is a spectral domain (SD) type apparatus using a broadband white light source. Due to the optical tomography apparatus of the present invention, it is possible for the first time to realize capturing of a two-dimensional spectroscopic tomographic image in the ultraviolet region in a non-destructive and non-invasive natural state (in-vivo, in-situ) for keratin, epidermis, and upper dermis of human skin. Since the depth distribution can be acquired from the spectrum, a mechanical scan for changing the optical path length is not necessary unlike a time domain (TD) type. By adopting the cylindrical lens of the emission optical system, the emission of sample light on the measurement surface is performed in a line shape. In addition, an objective lens of a cylindrical lens perpendicular thereto is provided. Therefore, scanning in the surface direction at the time of acquiring the two-dimensional spectroscopic tomographic image is not necessary. Since an optical tomographic image can be acquired by one emission of line-shaped sample light without performing a scan using sample light, it is also possible to measure a blurred sample such as human skin.

In addition, it is possible to acquire a tomographic image by easily extracting light in an arbitrary wavelength region in the ultraviolet region from the light emitted from the white light source as using the spectrum shaping unit.

By acquiring a two-dimensional spectroscopic tomographic image as using ultraviolet light, it is possible to evaluate the penetration depth of ultraviolet light for the measurement target. In addition, by acquiring optical tomographic images in other wavelength regions (ultraviolet region or visible region) simultaneously or sequentially, it is possible to evaluate the difference in penetration depth due to wavelength by comparing the both.

An embodiment of a light penetration depth evaluation method of the present invention using the optical tomography apparatus of the present embodiment will be described.

The light penetration depth evaluation method of the first embodiment is a method of cutting out an arbitrary wavelength region in the ultraviolet region from low coherent light, which is emitted from the single light source 11 and which includes a wavelength region from an ultraviolet region to a visible region, and shaping the arbitrary wavelength region into a spectrum having an arbitrary wavelength width, splitting the low coherent light $L_0$ having the shaped spectrum into the sample light $L_1$ and the reference light $L_2$, emitting the sample light $L_1$ to the measurement target S in a line shape, generating the interference light $L_4$ by superimposing the reflected light $L_3$ from the measurement target S due to emission of the sample light $L_1$ and the reference light $L_2$ on each other, acquiring a two-dimensional spectroscopic tomographic image of the measurement target S by spectroscopically detecting the interference light $L_4$ and performing frequency analysis, and evaluating the penetration depth of the sample light $L_0$ for the measurement target S based on the acquired two-dimensional spectroscopic tomographic image.

The light penetration depth can be evaluated, for example, by displaying a spectroscopic tomographic image on the image display device. As described above, if the scale is displayed on or in the vicinity of the two-dimensional spectroscopic tomographic image, it is possible to measure the penetration depth (how deep a region (region from which light returns after reaching the inside) having a signal is in the tomographic image) by visual observation. Alternatively, the penetration depth may be measured from the two-dimensional tomographic image (data) by calculation.

A light penetration depth evaluation method of a second embodiment will be described. The light penetration depth evaluation method of the second embodiment is a method of first acquiring a two-dimensional spectroscopic tomographic image, which is obtained by low coherent light in an arbitrary wavelength region in the ultraviolet region having a shaped spectrum, as a first two-dimensional spectroscopic tomographic image in the same manner as in the evaluation method of the first embodiment described above, acquiring a second two-dimensional spectroscopic tomographic image by changing the amount of low coherent light in the same wavelength region, and evaluating the penetration depth of sample light for the measurement target based on the first two-dimensional spectroscopic tomographic image and the second two-dimensional spectroscopic tomographic image.

The light penetration depth can be evaluated in the same manner as in the case of the first embodiment. In addition, by simultaneously displaying the first and second two-dimensional spectroscopic tomographic images on the image display device, it is possible to easily recognize the difference in penetration depth between both images by visual observation. Quantitative discussion of what % of UV light should be cut to prevent ultraviolet light from penetrating beyond a certain depth of skin or film can be made by evaluating the difference in penetration depth due to the amount of ultraviolet light.

A light penetration depth evaluation method of a third embodiment will be described. The light penetration depth evaluation method of the third embodiment is a method of setting, as a first wavelength region, an arbitrary wavelength region in the ultraviolet region having a shaped spectrum in the evaluation method of the first embodiment described above, acquiring a two-dimensional spectroscopic tomographic image based on low coherent light in the first wavelength region as a first two-dimensional spectroscopic tomographic image, cutting out a second wavelength region, which is different from the first wavelength region, from low coherent light, which is emitted from a single light source and which includes a wavelength region from an ultraviolet region to a visible region, and shaping the second wavelength region into a spectrum having an arbitrary wavelength width, acquiring a second two-dimensional spectroscopic tomographic image based on low coherent light in the second wavelength region, and evaluating the penetration depth of each sample light beam for the measurement target based on the first two-dimensional spectroscopic tomographic image and the second two-dimensional spectroscopic tomographic image.

A light penetration depth evaluation method of a fourth embodiment will be described. The light penetration depth evaluation method of the fourth embodiment is a method of cutting out a second wavelength region different from the first wavelength region and shaping the second wavelength region into a second spectrum having an arbitrary wavelength width at the same time as when cutting out an arbitrary wavelength region in the ultraviolet region from low coherent light, which is emitted from the single light source and which includes a wavelength region from an ultraviolet region to a visible region, as the first wavelength region in the evaluation method of the first embodiment, acquiring a second two-dimensional spectroscopic tomographic image as using the low coherent light in the second wavelength region having the second spectrum at the same time as when acquiring the two-dimensional spectroscopic tomographic image as a first two-dimensional spectroscopic tomographic image as using the low coherent light in the first wavelength region in the evaluation method of the first embodiment, and evaluating the penetration depth of each sample light beam for the measurement target based on the first two-dimensional spectroscopic tomographic image and the second two-dimensional spectroscopic tomographic image.

In the third embodiment, two-dimensional spectroscopic tomographic images are sequentially acquired as using low coherent light beams with different wavelength regions. Meanwhile, the fourth embodiment is different from the third embodiment in that two-dimensional spectroscopic tomographic images are acquired simultaneously, but the same images can be acquired as the first and second two-dimensional spectroscopic tomographic images.

In the third and fourth embodiments, the light penetration depth can be evaluated in the same manner as in the case of the first embodiment. In addition, by simultaneously displaying the first and second two-dimensional spectroscopic tomographic images on the image display device, it is possible to easily recognize the difference in penetration depth between both images by visual observation. By evaluating the difference in penetration depth due to the difference in the wavelength region, it is possible to present guidelines for cosmetics or the like so that unwanted light is cut but other light beams are not cut. For example, a cosmetic product that cuts UV light and captures visible light into the skin without cutting the visible light can be mentioned.

In the third and fourth embodiments, the second wavelength region may be either an ultraviolet region or a visible region as long as the second wavelength region is a wavelength region different from the first wavelength region.

Figure 4A:
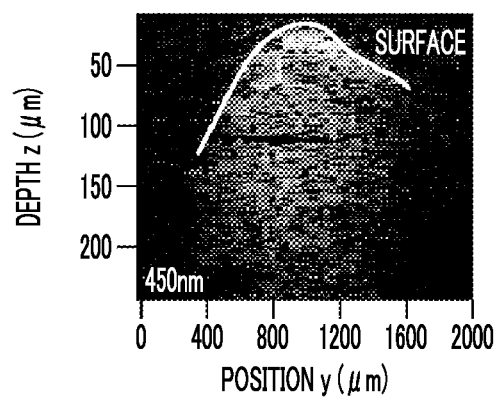
FIG. 4A is a two-dimensional spectral image of human skin captured at 450 nm.
Figure 4B:
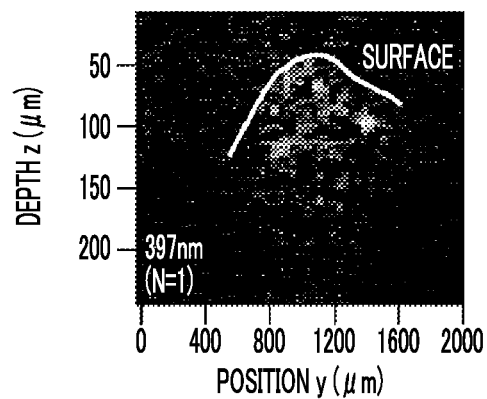
FIGS. 4B to 4D are two-dimensional spectral images of human skin captured at 397 nm (FIG. 4D is a case where a glass plate coated with an ultraviolet inhibitor is inserted on the optical path of ultraviolet light between the human skin and an apparatus).
Figure 4C:
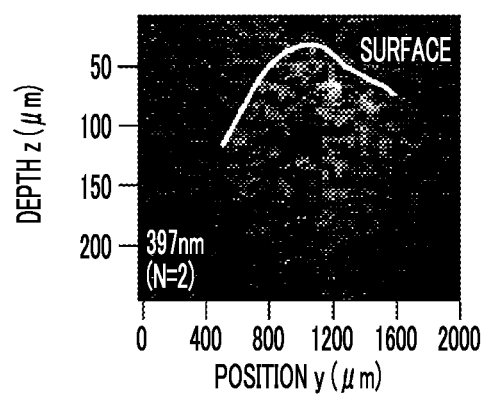
Figure 4D:
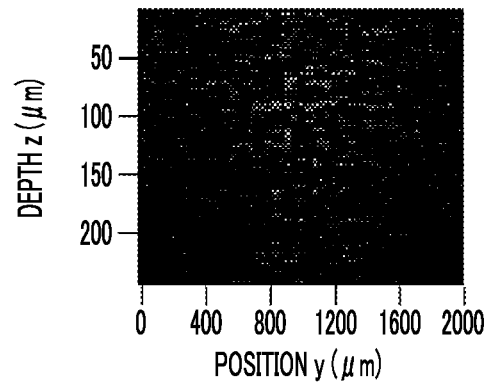

FIGS. 4A to 4D are spectroscopic tomographic images of human skin obtained by using a spectrum that is shaped by cutting out a predetermined wavelength region from super continuum light in the optical tomography apparatus of the present embodiment. In FIG. 4A, a spectroscopic tomographic image of human skin was acquired by using low coherent light having a Gaussian distribution spectrum with a peak wavelength of 450 nm and a wavelength width of 20 nm. In FIGS. 4B to 4D, a spectroscopic tomographic image of human skin was acquired by using low coherent light having a Gaussian distribution spectrum with a peak wavelength of 397 nm and a wavelength width of 5 nm.

FIGS. 4A, 4B, and 4C are images obtained by direct imaging of human skin, and FIG. 4D is an image obtained by imaging human skin in a state in which a glass plate coated with ultraviolet absorber is disposed on the optical path of sample light between the OCT apparatus and the human skin. The images shown in FIGS. 4A, 4B, 4C, and 4D were captured at different times, but were not acquired at the same time. In FIGS. 4B and 4C, measurement was performed under the same conditions.

From FIGS. 4A, 4B, and 4C, it can be seen that the amount of ultraviolet light returning from the inside of the skin is smaller than the amount of visible light returning from the inside of the skin and that the light scatters back to the depth of about 100 µm. It is thought that a reduction in the amount of light returning from the inside of the skin is due to the influence of absorption by melanin pigment present in the epidermis. Since ultraviolet light reaching the inside of the skin damages the skin, development of products that reduce the amount of light incident on the skin has been required for cosmetic development.

From FIG. 4D, it can be seen that ultraviolet light is blocked by arranging the UV absorber in the optical path and accordingly the UV light is prevented from being incident on the inside of the skin.

In the time domain type imaging apparatus, since scanning in the depth direction is mechanically performed, it takes several minutes to acquire a two-dimensional spectroscopic tomographic image. For this reason, it has been impossible to obtain a good tomographic image of a measurement target causing blurring or vibration, such as human skin. In the optical tomography apparatus of the present invention, since it is possible to perform imaging with an extremely short (for example, 20 ms) exposure, it is possible to acquire a good optical tomographic image of the actual human skin.

The measurement target of the apparatus of the present invention is not limited to human skin, and the apparatus of the present invention can also be used to obtain material distribution information in the thickness direction of a thin film material or the like.

Figure 5A:
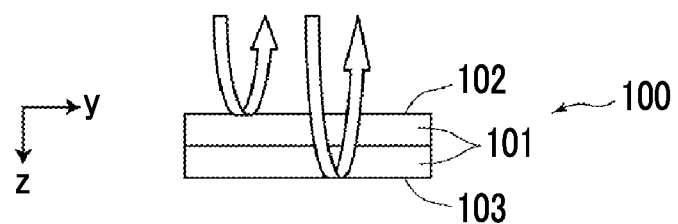
FIG. 5A is a cross-sectional view of a two-layer structure that is a measurement target.

A case where the measurement target is cover glass will be described with reference to FIGS. 5A and 5B. FIG. 5A is a cross-section of cover glass 100 to be measured. The cover glass 100 has a two-layer structure in which two sheets of cover glass 101 having a thickness of 170 µm are superimposed with a matching oil interposed therebetween. When sample light is made incident from a top surface 102 of the cover glass 100, reflected light is generated on the top surface 102 and a bottom surface 103.

Figure 5B:
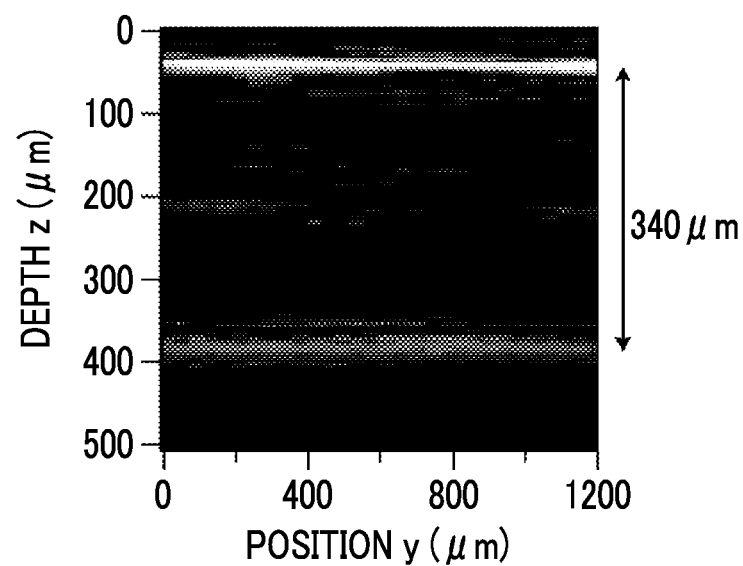
FIG. 5B is a two-dimensional spectroscopic tomographic image of the cover glass shown in FIG. 5A.

FIG. 5B is a two-dimensional spectroscopic tomographic image of the cover glass 101 acquired with an exposure time of 1 s as using a Gaussian distribution spectrum, which is shaped by cutting out a wavelength in the ultraviolet region from super continuum light and has a peak wavelength of 397 nm and a wavelength width of 5 nm, in the optical tomography apparatus of the present embodiment. As shown in FIG. 5B, the positions of the top and bottom surfaces of the cover glass are shown clearly in white, and the thickness of 340 µm can be measured. Although this diagram is a cover glass measurement result, it is naturally possible to measure the film.

Assuming that the measurement target is an ultraviolet absorbing film or the like, the amount of reflection on the bottom surface decreases as the amount of ultraviolet light absorbed therein increases. Therefore, it is possible to evaluate the effect from the two-dimensional tomographic image. Depending on whether or not the bottom surface reflection of the film is visible, it is possible to evaluate whether or not UV light penetrates up to the depth (film thickness).

A specific example of the light penetration depth evaluation method of the fourth embodiment will be described in which the light penetration depth is evaluated by acquiring a plurality of spectroscopic tomographic images of the same place at the same time as using a spectrum having a plurality of different wavelength regions.

Figure 6:
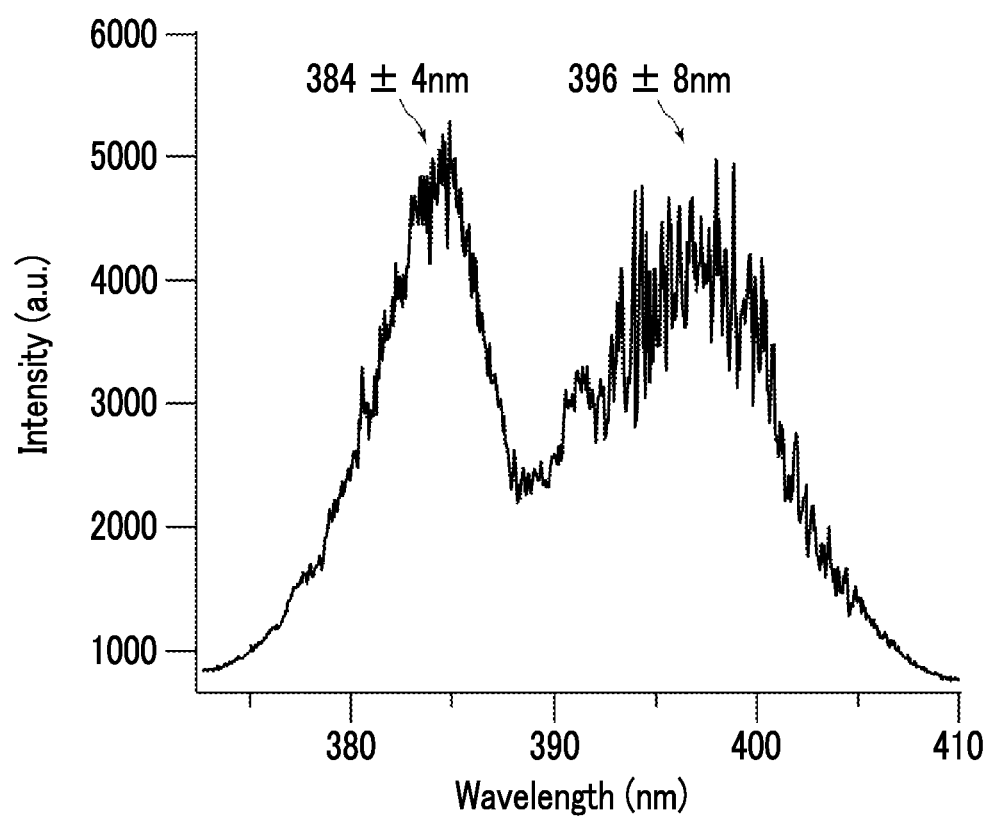
FIG. 6 is a diagram showing a Gaussian distribution spectrum shaped by cutting out two different wavelength regions in an ultraviolet region from light having the profile shown in FIG. 2.

First, FIG. 6 shows a spectrum shaped by cutting out two different wavelength regions in the ultraviolet region from light having the profile shown in FIG. 2.

The spectrum shown in FIG. 6 includes a spectrum having a center wavelength of 384 nm and a wavelength width of 4 nm in a first wavelength region from 373 nm to 389 nm in wavelength and a spectrum having a center wavelength of 396 nm and a wavelength width of 8 nm in a second wavelength region from 389 nm to 410 nm in wavelength.

By acquiring a spectroscopic tomographic image from each interference spectrum of light in two wavelength regions as described above, it is possible to acquire tomographic images having different wavelength regions at the same time by one measurement.

Figure 7A:
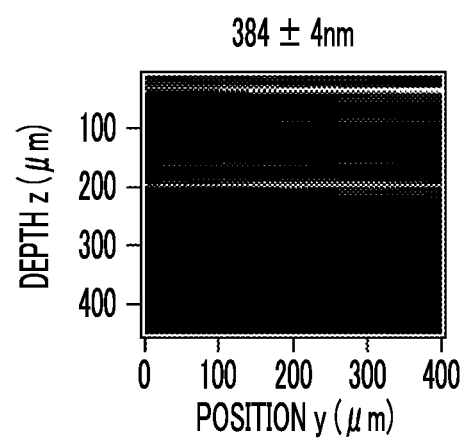
FIG. 7A is a spectroscopic tomographic image of cover glass that is acquired as using light having a spectrum of 384±4 nm based on simultaneous and same-place measurement.
Figure 7B:
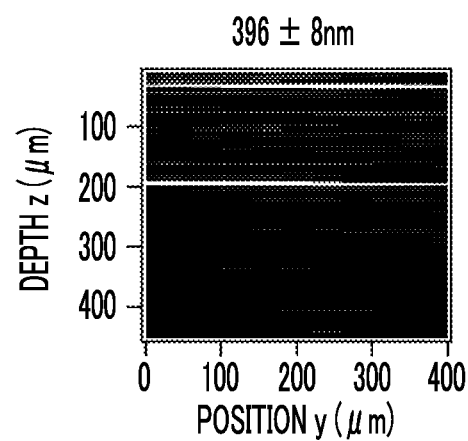
FIG. 7B is a spectroscopic tomographic image of cover glass that is acquired as using light having a spectrum of 396±8 nm based on simultaneous and same-place measurement.

FIGS. 7A and 7B show spectroscopic tomographic images of cover glass acquired by performing simultaneous and same-place measurement as using light in two different wavelength regions in the ultraviolet region shown in FIG. 6 with the cover glass as a measurement target. FIG. 7A is a spectroscopic tomographic image acquired as using a spectrum of 384±4 nm, and FIG. 7B is a spectroscopic tomographic image acquired as using a spectrum of 396±8 nm.

The thickness of the cover glass is 170 nm. In each spectroscopic tomographic image, the upper line of two white lines is due to top surface reflection of the cover glass, and the lower line is due to bottom surface reflection of the cover glass. In both images, the distance between the two white lines is about 170 nm, which is almost equal to the thickness of the cover glass. Therefore, it was theoretically confirmed that a tomographic image could be correctly measured even in the multi-wavelength simultaneous measurement.

Figure 8A:
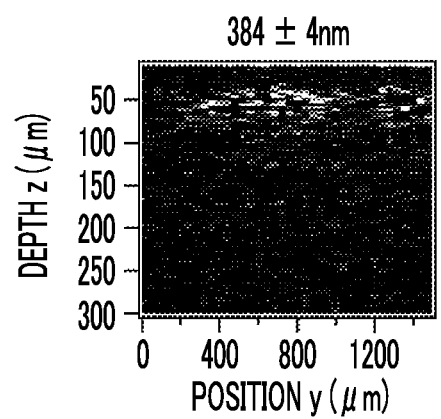
FIG. 8A is a spectroscopic tomographic image of paper that is acquired as using light having a spectrum of 384±4 nm based on simultaneous and same-place measurement.
Figure 8B:
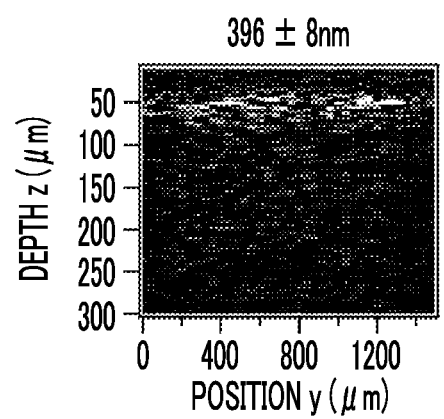
FIG. 8B is a spectroscopic tomographic image of paper that is acquired as using light having a spectrum of 396±8 nm based on simultaneous and same-place measurement.

FIGS. 8A and 8B show spectroscopic tomographic images of paper (business card) acquired by performing simultaneous and same-place measurement as using light in two different wavelength regions in the ultraviolet region shown in FIG. 6 with the paper as a measurement target. FIG. 8A is a spectroscopic tomographic image acquired as using a spectrum of 384±4 nm, and FIG. 8B is a spectroscopic tomographic image acquired as using a spectrum of 396±8 nm.

It was confirmed that simultaneous and same-place measurement of the tomographic image of paper could be performed at two different wavelengths in the ultraviolet region. Although the image quality is not good in the measurement of the measurement number of times N=1, scattering from a deep region tends to be large in the case of using light having a center wavelength of 396 nm and a wavelength width of 8 nm shown in FIG. 8B.

In the above explanation, an example has been described in which simultaneous and same-place imaging is performed as using two different wavelength regions in the ultraviolet region. However, it is also possible to perform simultaneous and same-place imaging as using two wavelength regions of a wavelength region in the ultraviolet region and a wavelength region in the visible region in the same manner as described above.

Next, a specific example of the light penetration depth evaluation method of the third embodiment will be described in which the light penetration depth is evaluated by acquiring a plurality of spectroscopic tomographic images by changing the amount of light as using a spectrum having the same wavelength region in the ultraviolet region.

Figure 9A:
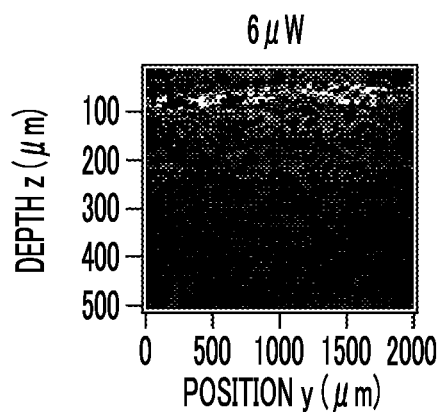
FIG. 9A is a spectroscopic tomographic image of paper that is acquired with the amount of emitted light of 6 μW as using light having the same wavelength region in the ultraviolet region.
Figure 9B:
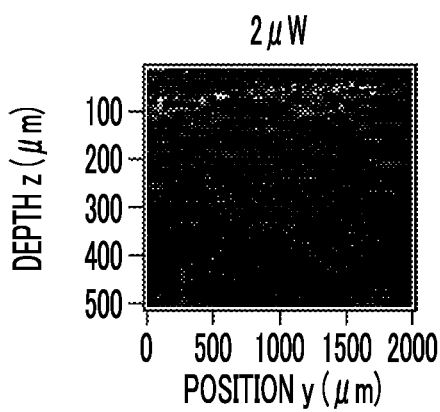
FIG. 9B is a spectroscopic tomographic image of paper that is acquired with the amount of emitted light of 2 μW as using light having the same wavelength region in the ultraviolet region.
Figure 9C:
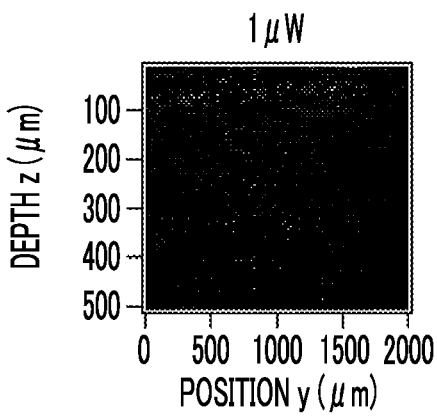
FIG. 9C is a spectroscopic tomographic image of paper that is acquired with the amount of emitted light of 1 μW as using light having the same wavelength region in the ultraviolet region.

FIGS. 9A, 9B, and 9C are spectroscopic tomographic images that are acquired, with the each amounts of light emitted to the measurement target to which 6 µW, 2 µW are set, and 1 µW, using light (397±5 nm spectrum) having the same wavelength region in the ultraviolet region when the measurement target is paper (business card).

From FIG. 9, it was confirmed that the degree of arrival of UV light was increased corresponding to increasing the amount of light emitted to the measurement target from 1 µW to 2 µW and 6 µW.

By using a light penetration depth measuring method using the optical tomography apparatus of the present invention, it is possible to evaluate the penetration depth of ultraviolet light before and after application of chemicals, such as cosmetics, quasi-drugs, and medicines, onto human skin and to examine their performances accurately.

According to the apparatus and the method of the present invention, since arbitrary wavelengths in the ultraviolet region can be cut out by the spectrum shaping unit, it is also possible to quantify the effect of protection capability of chemicals against the UV-A wavelength (315 to 400 nm) and the UV-B wavelength (280 to 315 nm) in the ultraviolet region. In addition, by providing a variable ND filter in the emission optical system, it is possible to adjust the amount of emission of sample light. Accordingly, since it is possible to measure the depth of penetration of ultraviolet light into the skin in a case where the amount of light is changed, it is possible to quantify the effect of protection capability of cosmetics, quasi-drugs, and medicines for the amount of ultraviolet light.

Specifically, the results of measurement of the UV light penetration depth before and after applying cosmetics to the model skin will be described.

Figure 10A:
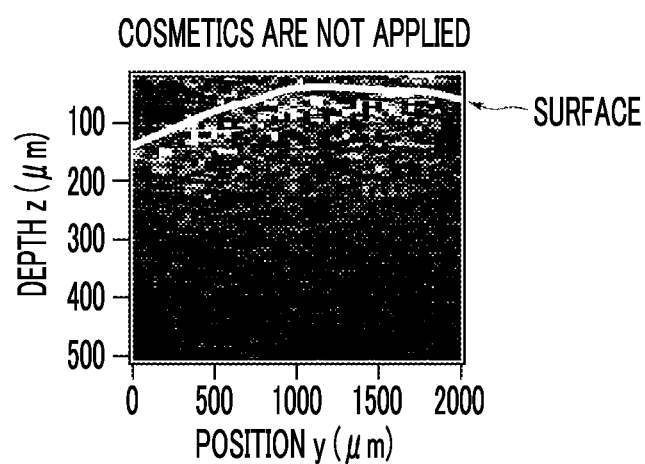
FIG. 10A is a spectroscopic tomographic image captured before applying cosmetics to the model skin.
Figure 10B:
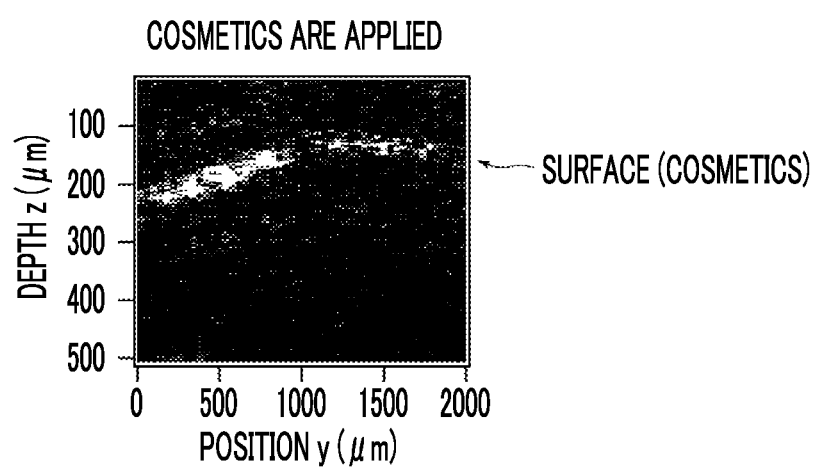
FIG. 10B is a spectroscopic tomographic image captured after applying cosmetics to the model skin.

FIG. 10A shows a spectroscopic tomographic image captured before applying cosmetics to the model skin, and FIG. 10B shows a spectroscopic tomographic image captured after applying cosmetics to the model skin B. Here, the spectroscopic tomographic images were captured as using ultraviolet light having a spectrum of 397±5 nm. In FIGS. 10A and 10B, surface positions in the direction of depth z are different. In FIG. 10B, it is estimated that a portion shining white is a reflection from the cosmetic layer applied on the model skin surface. Cosmetic materials contain particles that scatter light. Accordingly, since UV light is strongly scattered by the particles, it can be considered that a strong signal is observed. On the other hand, in FIG. 10A, it was observed that scattering and reflection on the surface of the skin was weak and that light penetrated up to about 200 µm in the depth direction from the surface.

That is, it was possible to observe that UV light was scattered and absorbed on the surface by applying cosmetics and accordingly light did not penetrate to the inside.

What is claimed is:

1. A light penetration depth evaluation method using an optical tomography method of splitting low coherent light into sample light and reference light, emitting the sample light to a measurement target in a line shape, generating interference light by superimposing reflected light from the measurement target due to emission of the sample light and the reference light on each other, and acquiring a two-dimensional spectroscopic tomographic image of the measurement target by spectroscopically detecting the interference light and performing frequency analysis, the method comprising:

cutting out an arbitrary wavelength region in an ultraviolet region from low coherent light, which is emitted from a single light source and which includes a wavelength region from an ultraviolet region to a visible region, and shaping the arbitrary wavelength region into a spectrum having an arbitrary wavelength width;

acquiring the two-dimensional spectroscopic tomographic image as using the low coherent light in the arbitrary wavelength region having the spectrum; and evaluating a penetration depth of the sample light for the measurement target based on the two-dimensional spectroscopic tomographic image.

2. The light penetration depth evaluation method according to claim 1, wherein, after the two-dimensional spectroscopic tomographic image based on the low coherent light in the arbitrary wavelength region in the ultraviolet region having the spectrum is acquired as a first two-dimensional spectroscopic tomographic image, a second two-dimensional spectroscopic tomographic image is acquired by changing an amount of low coherent light in the arbitrary wavelength region, and the penetration depth of the sample light for the measurement target is evaluated based on the first two-dimensional spectroscopic tomographic image and the second two-dimensional spectroscopic tomographic image.

3. The light penetration depth evaluation method according to claim 1, wherein the arbitrary wavelength region in the ultraviolet region is set as a first wavelength region, the spectrum is set as a first spectrum, and the two-dimensional spectroscopic tomographic image based on the low coherent light in the arbitrary wavelength region in the ultraviolet region is set as a first two-dimensional spectroscopic tomographic image, a second wavelength region different from the first wavelength region is cut out from low coherent light, which is emitted from the single light source and which includes a wavelength region from the ultraviolet region to the visible region, and the second wavelength region is shaped into a second spectrum having an arbitrary wavelength width, a second two-dimensional spectroscopic tomographic image based on the low coherent light in the second wavelength region having the second spectrum is acquired, and the penetration depth of the sample light for the measurement target is evaluated based on the first two-dimensional spectroscopic tomographic image and the second two-dimensional spectroscopic tomographic image.

4. The light penetration depth evaluation method according to claim 1, wherein, at the same time as when cutting out an arbitrary wavelength region in the ultraviolet region from low coherent light including a wavelength region from the ultraviolet region to the visible region and shaping the arbitrary wavelength region into a spectrum having an arbitrary wavelength width, a second wavelength region different from a first wavelength region is cut out and the second wavelength region is shaped into a second spectrum having an arbitrary wavelength width with the arbitrary wavelength region as the first wavelength region and the spectrum as a first spectrum, a second two-dimensional spectroscopic tomographic image is acquired as using low coherent light in the second wavelength region having the second spectrum at the same time as when acquiring the two-dimensional spectroscopic tomographic image as a first two-dimensional spectroscopic tomographic image as using low coherent light in the first wavelength region, and the penetration depth of the sample light for the measurement target is evaluated based on the first two-dimensional spectroscopic tomographic image and the second two-dimensional spectroscopic tomographic image.

5. A light penetration depth evaluation method using an optical tomography method of splitting low coherent light into sample light and reference light, emitting the sample light to a measurement target in a line shape, generating interference light by superimposing reflected light from the measurement target due to emission of the sample light and the reference light on each other, and acquiring a two-dimensional spectroscopic tomographic image of the measurement target by spectroscopically detecting the interference light and performing frequency analysis, the method comprising:

cutting out an arbitrary wavelength region from low coherent light, which is emitted from a single light source and which includes a wavelength region from an ultraviolet region to a visible region, and shaping the arbitrary wavelength region into a spectrum having single or plural arbitrary wavelength widths to acquire a first two-dimensional spectroscopic tomographic image, which is based on low coherent light in a first wavelength region in an ultraviolet region, and a second two-dimensional spectroscopic tomographic image, which is based on low coherent light in a second wavelength region different from the first wavelength region or based on low coherent light in the first wavelength region having a light amount different from the low coherent light in the first wavelength region, simultaneously or sequentially; and evaluating a penetration depth of the sample light for the measurement target based on the first two-dimensional spectroscopic tomographic image and the second two-dimensional spectroscopic tomographic image.

6. The light penetration depth evaluation method according to claim 3,
wherein the second wavelength region is an ultraviolet wavelength region.

7. The light penetration depth evaluation method according to claim 4,
wherein the second wavelength region is an ultraviolet wavelength region.

8. The light penetration depth evaluation method according to claim 5,
wherein the second wavelength region is an ultraviolet wavelength region.

9. The light penetration depth evaluation method according to claim 3,
wherein the second wavelength region is a visible wavelength region.

10. The light penetration depth evaluation method according to claim 4,
wherein the second wavelength region is a visible wavelength region.

11. The light penetration depth evaluation method according to claim 5,
wherein the second wavelength region is a visible wavelength region.

12. A performance test method, comprising:
testing a performance of chemicals by evaluating a penetration depth of light in an ultraviolet region before and after application of the chemicals to human skin, which is a measurement target, as using the light penetration depth evaluation method according to claim 1.

13. A performance test method, comprising:
testing a performance of chemicals by evaluating a penetration depth of light in an ultraviolet region before and after application of the chemicals to human skin, which is a measurement target, as using the light penetration depth evaluation method according to claim 5.

14. An optical tomography apparatus, comprising:
a light source unit that has a single light source, which emits low coherent light including a wavelength region from an ultraviolet region to a visible region, and a spectrum shaping unit, which cuts an arbitrary wavelength region in the ultraviolet region from light emitted from the light source and shapes the arbitrary wavelength region into a spectrum having an arbitrary wavelength width, and that emits low coherent light after the spectrum shaping;
a light splitting unit that splits the low coherent light emitted from the light source unit into sample light and reference light;
a sample light emission optical system that emits the sample light to a measurement target in a line shape;
a multiplexing unit that superimposes reflected light from the measurement target when the sample light is emitted to the measurement target and the reference light on each other;
an interference light detection unit that spectroscopically detects interference light between the reflected light and the reference light multiplexed by the multiplexing unit; and
a tomographic image acquisition unit that acquires a two-dimensional spectroscopic tomographic image of the measurement target by performing frequency analysis of the interference light detected by the interference light detection unit.

15. The optical tomography apparatus according to claim 14, further comprising:
a measurement unit that calculates a penetration depth of the sample light for the measurement target from the two-dimensional spectroscopic tomographic image.

16. The optical tomography apparatus according to claim 14,
wherein, at the same time as when cutting out an arbitrary wavelength region in the ultraviolet region from low coherent light including a wavelength region from the ultraviolet region to the visible region and shaping the arbitrary wavelength region into a spectrum having an arbitrary wavelength width, the spectrum shaping unit cuts out a second wavelength region different from a first wavelength region and shaping the second wavelength region into a second spectrum having an arbitrary wavelength width with the arbitrary wavelength region as the first wavelength region and the spectrum as a first spectrum, and
the tomographic image acquisition unit acquires a second two-dimensional spectroscopic tomographic image as using low coherent light in the second wavelength region having the second spectrum at the same time as when acquiring the two-dimensional spectroscopic tomographic image as a first two-dimensional spectroscopic tomographic image as using low coherent light in the first wavelength region.

17. The optical tomography apparatus according to claim 14, further comprising:
a display unit that displays the two-dimensional spectroscopic tomographic image.

18. The optical tomography apparatus according to claim 14,
wherein the sample light emission optical system comprises a variable neutral density filter.

19. The optical tomography apparatus according to claim 14,
wherein the sample light emission optical system comprises a cylindrical lens, and a cylindrical lens disposed perpendicular to the cylindrical lens is provided between the multiplexing unit and the interference light detection unit.

20. The optical tomography apparatus according to claim 14,
wherein the light source is a super continuum light source.

* * * * *